United States Patent
Diehl et al.

(10) Patent No.: US 7,150,809 B2
(45) Date of Patent: Dec. 19, 2006

(54) THERMAL SEPARATING PROCESS

(75) Inventors: Volker Diehl, Ellerstadt (DE); Ulrich Jaeger, Roemerberg (DE); Ulrich Hammon, Mannheim (DE); Juergen Schroeder, Ludwigshafen (DE); Steffen Rissel, Kirchheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 204 days.

(21) Appl. No.: 10/823,672

(22) Filed: Apr. 14, 2004

(65) Prior Publication Data

US 2004/0206617 A1   Oct. 21, 2004

Related U.S. Application Data

(60) Provisional application No. 60/476,161, filed on Jun. 6, 2003.

(30) Foreign Application Priority Data

Apr. 15, 2003   (DE) .................. 103 17 436

(51) Int. Cl.
*B01D 3/00* (2006.01)
(52) U.S. Cl. .................. 203/8; 203/90; 203/100; 203/DIG. 21; 562/600
(58) Field of Classification Search .......... 203/8, 203/90, DIG. 21, 100; 202/158; 261/115, 261/114.5; 562/600
See application file for complete search history.

(56) References Cited

U.S. PATENT DOCUMENTS

| | | | |
|---|---|---|---|
| 2,267,929 A | 12/1941 | Lefebure et al. | |
| 5,262,094 A * | 11/1993 | Chuang et al. | 261/97 |
| 5,407,605 A * | 4/1995 | Resetarits et al. | 261/98 |
| 5,788,895 A | 8/1998 | Altinger et al. | |
| 5,831,124 A | 11/1998 | Machhammer et al. | |
| 6,267,359 B1 | 7/2001 | Stippick | |
| 6,294,056 B1 | 9/2001 | Matsumoto et al. | |
| 6,409,886 B1 | 6/2002 | Matsumoto et al. | |
| 6,413,379 B1 | 7/2002 | Machhammer et al. | |
| 6,654,124 B1 | 11/2003 | Morris et al. | |
| 2001/0007043 A1 | 7/2001 | Machhammer et al. | |
| 2001/0025122 A1 | 9/2001 | Hirao et al. | |
| 2003/0028052 A1 | 2/2003 | Hirao et al. | |
| 2004/0116736 A1 | 6/2004 | Machhammer et al. | |
| 2004/0138501 A1 | 7/2004 | Thiel et al. | |

FOREIGN PATENT DOCUMENTS

| | | |
|---|---|---|
| DE | 199 24 532 | 11/2000 |
| DE | 101 15 277 | 6/2002 |
| DE | 102 18 419 | 6/2003 |
| DE | 102 24 341 | 7/2003 |
| DE | 103 00 816 | 7/2004 |
| EP | 196 06 877 | 8/1997 |

(Continued)

*Primary Examiner*—Virginia Manoharan
(74) *Attorney, Agent, or Firm*—Oblon, Spivak, McClelland, Maier & Neustadt, P.C.

(57) ABSTRACT

(Meth)acrylic monomers are separated by a thermal separation process by ascending at least one ascending gaseous stream in a separating column containing a sequence of mass transfer trays and a liquid stream that contains dissolved polymerization inhibitor which descends in the separating column, and in at least one of the streams being (meth) acrylic monomers; and spraying the inner surface of the separating column with the descending liquid stream that contains the dissolved polymerization inhibitor, and the separating column having internals, certain areas of which are shadow regions of the sprayed descending liquid stream; and which shadow regions are equipped by covering means which prevent contact of the shadow regions with (meth) acrylic monomers and consequently undesired polymerization of monomer.

11 Claims, 3 Drawing Sheets

FOREIGN PATENT DOCUMENTS

| | | |
|---|---|---|
| EP | 0 937 488 | 8/1999 |
| EP | 0 982 287 | 3/2000 |
| EP | 982 289 | 3/2000 |
| EP | 1 044 957 | 10/2000 |
| EP | 11 25 912 | 8/2001 |
| GB | 514267 | 11/1939 |

* cited by examiner

THERMAL SEPARATING PROCESS

This application claims the benefit under Title 35, United States Code § 120 of the U.S. Provisional Application No. 60/476,161, filed Jun. 6, 2003.

BACKGROUND OF THE INVENTION

1. Field of the Invention

The present invention relates to a thermal separating process between at least one gaseous stream ascending in a separating column containing a sequence of mass transfer trays and a liquid stream descending in the separating column and comprising dissolved polymerization inhibitor, at least one of said streams comprising (meth)acrylic monomers, and the inner surface of the separating column being sprayed with the liquid stream descending in the separating column and comprising dissolved polymerization inhibitor, and the separating column having internals of whose surface at least parts are in the shadow region of the sprayed descending liquid stream.

2. Description of the Background

In this document, the notation (meth)acrylic monomers is an abbreviation of "acrylic monomers and/or methacrylic monomers".

In this document, the term acrylic monomers is an abbreviation of "acrolein, acrylic acid and/or esters of acrylic acid".

In this document, the term methacrylic monomers is an abbreviation of "methacrolein, methacrylic acid and/or esters of methacrylic acid".

In particular, the (meth)acrylic monomers addressed in this document are intended to include the following (meth)acrylic esters: methyl acrylate, methyl methacrylate, n-butyl acrylate, iso-butyl acrylate, iso-butyl methacrylate, n-butyl methacrylate, tert-butyl acrylate, tert-butyl methacrylate, ethyl acrylate, ethyl methacrylate, 2-ethylhexyl acrylate, 2-ethylhexyl methacrylate, N,N-dimethylaminoethyl acrylate, N,N-dimethylaminoethyl methacrylate, cyclohexyl methacrylate, 1,4-butanediol monoacrylate, hydroxyethyl acrylate, hydroxyethyl methacrylate, hydroxypropyl acrylate, hydroxypropyl methacrylate, glycidyl acrylate and glycidyl methacrylate.

As a consequence of their very reactive ethylenically unsaturated double bond, (meth)acrylic monomers are valuable starting compounds for preparing polymers which find use, for example, as adhesives, water-absorbing resin or as a binder for emulsion paints.

(Meth)acrolein and (meth)acrylic acid are prepared on the industrial scale predominantly by catalytic gas phase oxidation of suitable $C_3$–/$C_4$ precursor compounds (or of precursor compounds thereof), in particular of propene and propane in the case of acrolein and acrylic acid, or of isobutene and isobutane in the case of methacrylic acid and of methacrolein. However, other suitable starting substances in addition to propene, propane, isobutene and isobutane are other compounds containing 3 or 4 carbon atoms such as isobutanol, n-propanol or precursor compounds thereof, for example the methyl ether of isobutanol. (Meth)acrylic acid can also be obtained from (meth)acrolein.

A product gas mixture is normally obtained from which the (meth)acrylic acid or the (meth)acrolein has to be removed.

Esters of (meth)acrylic acid are obtainable, for example, by direct reaction of (meth)acrylic acid and/or (meth)acrolein with the appropriate alcohols. However, this case also results initially in generally liquid product mixtures from which the (meth)acrylic esters have to be removed (for example by rectification).

For the aforementioned removals, separating processes are frequently employed which are carried out in a separating column containing a sequence of mass transfer trays as separating internals. In these separating columns, gaseous (ascending) and liquid (descending) streams are in many cases conducted in countercurrent, and, as a consequence of the inequilibrium existing between the streams, there is heat and mass transfer which ultimately results in the desired separation in the separating column. In this document, such separating processes are to be referred to as thermal separating processes.

Examples of, and therefore an element of, the term "thermal separating processes" used in this document, are fractional condensation (cf. DE-A 19924532) and/or rectification (ascending vapor phase is conducted in countercurrent to descending liquid phase; the separating action is based on the vapor composition at equilibrium being different to the liquid composition), absorption (at least one ascending gas is conducted in countercurrent to at least one descending liquid; the separating action is based on the different solubility of the gas constituents in the liquid), stripping (like absorption; however, the liquid phase is laden with a component which is taken up by the stripping gas) and desorption (the reverse process to absorption; the gas dissolved in the liquid phase is removed by partial pressure reduction).

For example, the removal of (meth)acrylic acid or (meth)acrolein from the product gas mixture of the catalytic gas phase oxidation can be carried out in such a way that the (meth)acrylic acid or the (meth)acrolein is additionally basically removed by absorption into a solvent (for example water or an organic solvent) or by fractional condensation of the product gas mixture and the resulting condensate or absorbate is subsequently separated rectificatively (generally in a plurality of stages) to obtain more or less pure (meth)acrylic acid or (meth)acrolein (cf. for example, EP-A 717019, EP-A 1125912, EP-A 982289, EP-A 982287, DE-A 19606877, DE-A 1011527, DE-A 10224341 and DE-A 10218419).

The fractional condensation addressed above differs from the conventional rectification essentially in that the mixture to be separated is fed to the separating column in gaseous form (i.e. fully converted to the vapor form).

Instead of the fractional condensation, a total condensation can initially also be employed and the resulting condensates subsequently separated by rectification.

The gaseous or liquid mixtures which contain (meth)acrylic monomers and have already been addressed may contain the (meth)acrylic monomers either in more or less pure form or in dilution (for example with solvent or with diluent gases). The solvents may be either aqueous or an organic solvent, and the specific type of the organic solvent is substantially insignificant. The diluent gas may be, for example, nitrogen, carbon oxide (CO, $CO_2$), oxygen, hydrocarbon or a mixture of these gases.

This means, for example on the route to obtaining (meth)acryl monomers, thermal separating processes are applied in a highly differing manner to gaseous and/or liquid mixtures whose content of (meth)acrylic monomers may be $\geq 2\%$ by weight, or $\geq 10\%$ by weight, or $\geq 20\%$ by weight, or $\geq 40\%$ by weight, or $\geq 60\%$ by weight, or $\geq 80\%$ by weight, or $\geq 90\%$ by weight, or $\geq 95\%$ by weight, or $\geq 99\%$ by weight.

The (meth)acrylic monomers can accumulate either at the top or at the bottom of the separating column. However, it will be appreciated that fractions containing accumulated (meth)acrylic monomers can also be removed in the upper, lower or middle section of the separating column.

The mass transfer trays present in the separating columns for the thermal separating process fulfill the purpose of providing locations having continuous liquid phases in the separating column in the form of liquid layers. The surface of the vapor or gas stream ascending in the liquid layer and being distributed in the continuous liquid phase is then the decisive exchange surface.

The liquid flows over the mass transfer tray which has a multitude of passages. The gas ascends through these passages, so that the mass transfer process can take place. The reflux liquid is conducted further from tray to tray through the same orifices or through special drain apparatus (downcomers). The latter typically do not fall under the definition of the passage.

One problem area when carrying out thermal separating processes between at least one gaseous and at least one liquid stream, of which at least one comprises (meth)acrylic monomers, is that (meth)acrylic monomers are very reactive with regard to their free-radical polymerization and tend toward undesired polymerization.

It is therefore customary to operate the separating columns with polymerization inhibition. In other words, polymerization inhibitors (e.g. phenolic compounds, amino compounds, nitro compounds, phosphorus compounds, sulfur compounds, N-oxyl compounds and/or heavy metal salts are added to the liquid stream descending in the separating column (referred to in this document as reflux or reflux liquid).

All surfaces of the separating column which are wetted with the liquid stream descending in the separating column are thus automatically polymerization-inhibited.

With regard to the surfaces facing the liquid stream descending in the separating column (for example the upper side of the mass transfer trays), the aforementioned interaction is comparatively problem-free.

However, this no longer applies to those surfaces of the separating column which face away from the descending liquid stream (for example the underside of the mass transfer trays).

On these surfaces, (meth)acrylic monomers present unhibited in the ascending gaseous stream can condense out. The unhibited condensate (the polymerization tendency is particularly marked in the condensed phase as a consequence of the low intermolecular separation) can then polymerize, polymer which forms can accumulate and ultimately make the further operation of the separating column impossible.

EP-A 937488 and EP-A 1044957 therefore describe processes for rectifying mixtures comprising (meth)acrylic monomers, in which the inner surface of the rectification column, including the mass transfer tray underside, is sprayed with polymerization-inhibited reflux via nozzles.

DE-A 10300816 relates to thermal separating processes of mixtures comprising (meth)acrylic monomers, in which the separating column containing a sequence of mass transfer trays is operated in such a way that the gaseous stream moving upward, as it passes through the passages of the mass transfer trays, entrains small liquid droplets of the polymerization-inhibited liquid phase disposed thereon and sprays them upward.

A disadvantage of the procedures of EP-A 937488, EP-A 1044957 and DE-A 10300816 is that they can only achieve surface-covering spraying with polymerization-inhibited reflux at considerable cost and inconvenience.

In other words, there will always be parts of the surface of internals disposed in the separating column which neither face the descending polymerization-inhibited liquid stream nor are covered to a sufficient extent by sprayed polymerization-inhibited reflux.

Such parts of the surface are to be referred to in this document as parts of the surface which are in the shadow region of the sprayed (either via special nozzles and/or via mass transfer trays) descending liquid stream.

SUMMARY OF THE INVENTION

It is an object of the present invention to remove such parts of the surface of internals which are present in separating columns suitable for thermal separating processes and are in the shadow region of sprayed polymerization-inhibited reflux, in a very simple manner and without increased cost and inconvenience, in particular without spray nozzles to be used additionally, from the shadow region.

We have found that this object is achieved by a thermal separating process between at least one gaseous stream ascending in a separating column containing a sequence of mass transfer trays and a liquid stream descending in the separating column and comprising dissolved polymerization inhibitor, at least one of said streams comprising (meth) acrylic monomers, and the inner surface of the separating column being sprayed with the liquid stream descending in the separating column and comprising dissolved polymerization inhibitor, and the separating column having internals of whose surface at least parts are in the shadow region of the sprayed descending liquid stream, wherein parts of the surface of the internals which are in the shadow of the sprayed descending liquid stream are removed from the shadow region by being covered.

DETAILED DESCRIPTION OF THE PREFERRED EMBODIMENTS

In this document, a sequence of mass transfer trays refers to at least two, better at least three or at least four, successive mass transfer trays which are not interrupted by any other separating internals.

In processes according to the invention, the inner surface of the separating column is frequently sprayed with the liquid stream descending in the separating column by the gaseous stream moving upward, as it passes through mass transfer trays, entraining small liquid droplets of the liquid phase disposed thereon and spraying them upward.

The present invention is to be illustrated hereinbelow using examples without limiting its generality.

Frequently, the support elements installed in separating columns for thermal separating processes are double-T supports which extend from one side of the separating column to the other side of the separating column and are secured to the column wall.

In contrast to the simple T supports, as shown, for example, by EP-A 759316, double-T supports have increased load-bearing ability. Among other factors, this is linked to the fact that they have two transverse limbs, whereas the simple T support only has one transverse limb. The second transverse limb additionally strengthens the longitudinal limb.

Figure 1:
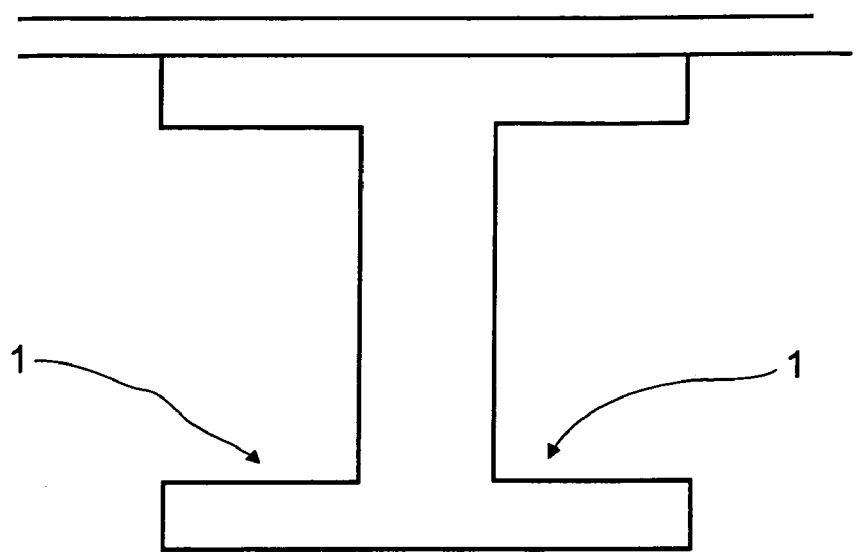
FIG. 1 is a cross-sectional view of a double T-support.

FIG. 1 shows the cross section of a double-T support with mass transfer tray resting thereon.

Figure 2:
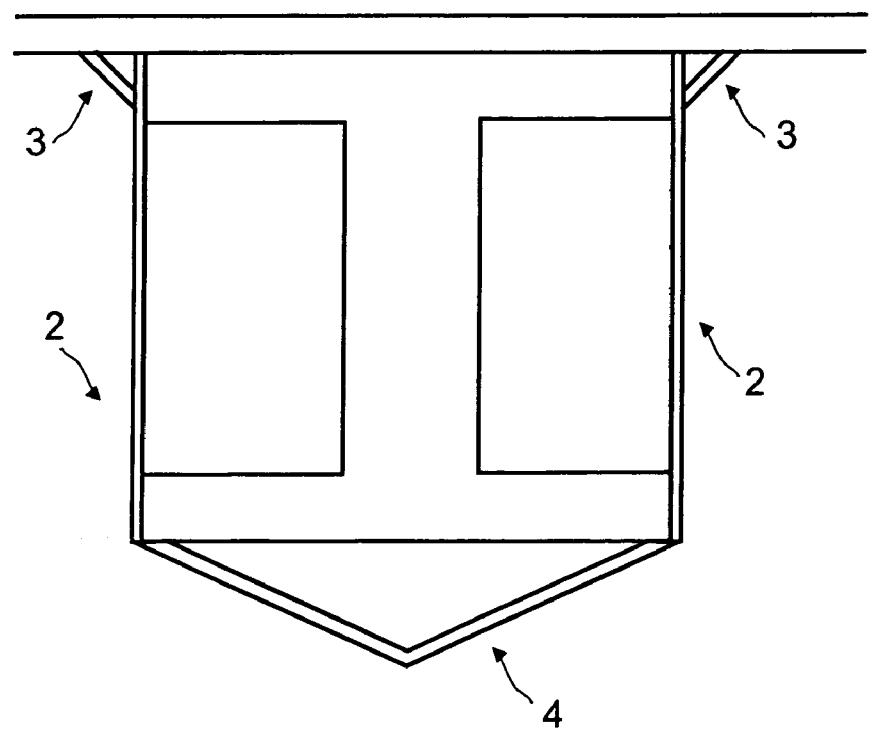
FIG. 2 is a cross-sectional view of a covered double T-support.

However, a disadvantage of double-T supports is that, for example, the parts of the surface of double-T supports which are indicated in FIG. 1 by the number (1) and are in the spray shadow of the liquid droplets which, as the gaseous stream moving upward passes through the passages of the mass transfer tray below, are entrained from the liquid phase present thereon and sprayed substantially vertically upward. FIG. 2 shows how this disadvantage can be remedied by simply mounting a cover (2), without an additional spray nozzle being required for polymerization-inhibited reflux.

The cover preferably also has the elements (3). They ease the draining of polymerization-inhibited liquid droplets which collect on the underside of the mass transfer tray resting on the double-T support and are sprayed upward from the mass transfer tray below. Any polymerization nuclei forming on the vertical cover wall are thus continuously washed away and transported into the column bottom. Polymerization inhibition is ensured.

It is also advantageous in accordance with the invention (4) when the cover also has a drip-off nose (4), since it reduces the residence time of reflux liquid as it drains off. However, the probability of polymerization increases with increasing residence time.

Figure 3:
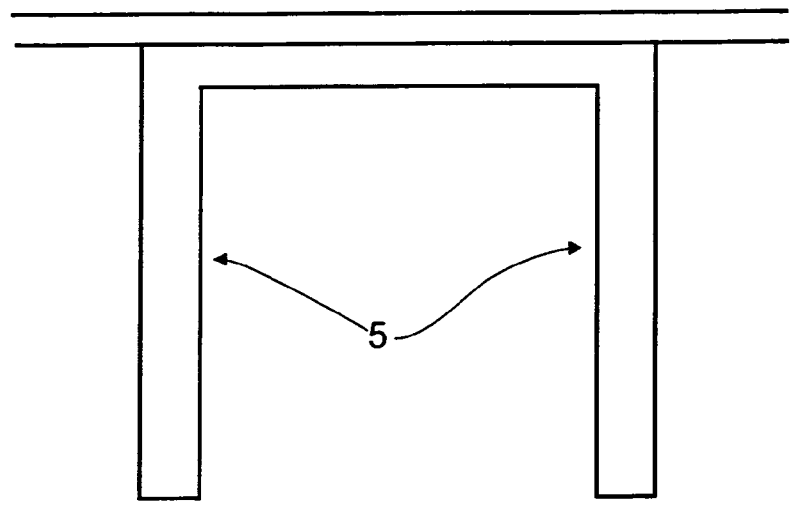
FIG. 3 is a cross-sectional view of a U-shaped support.
Figure 4:
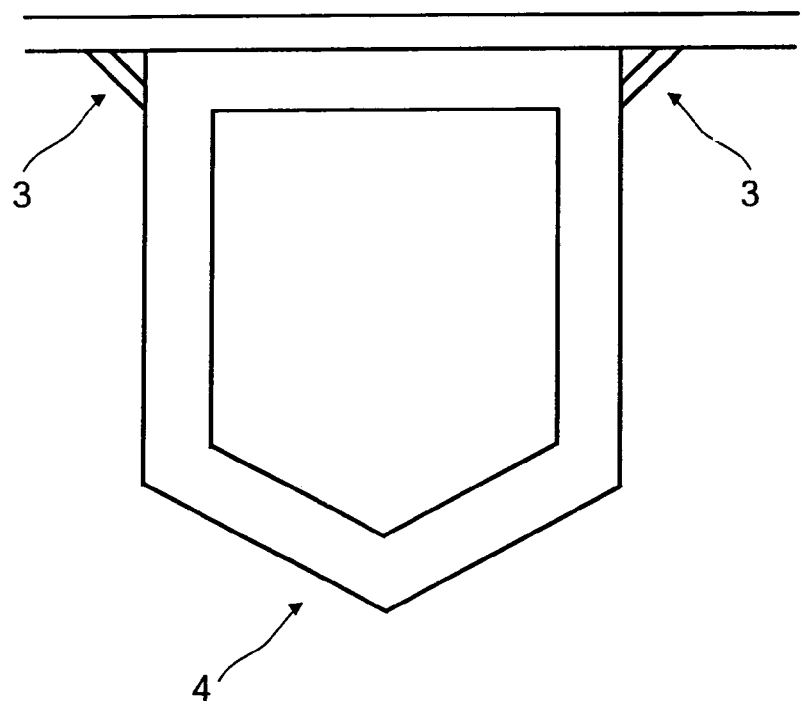
FIG. 4 is a cross-sectional view of a covered U-shaped support.

The same applies to U-shaped supports (since they have two longitudinal limbs, the longitudinal limbs can be shorter for the same load-bearing ability, which makes possible particularly small separations of the mass transfer trays), as shown by FIG. 3 with mass transfer tray resting thereon. In this case, for example, the vertical inner walls (5) are typical problem surfaces. FIG. 4 shows the solution to the problem in the form of an elegant cover.

Figure 5:
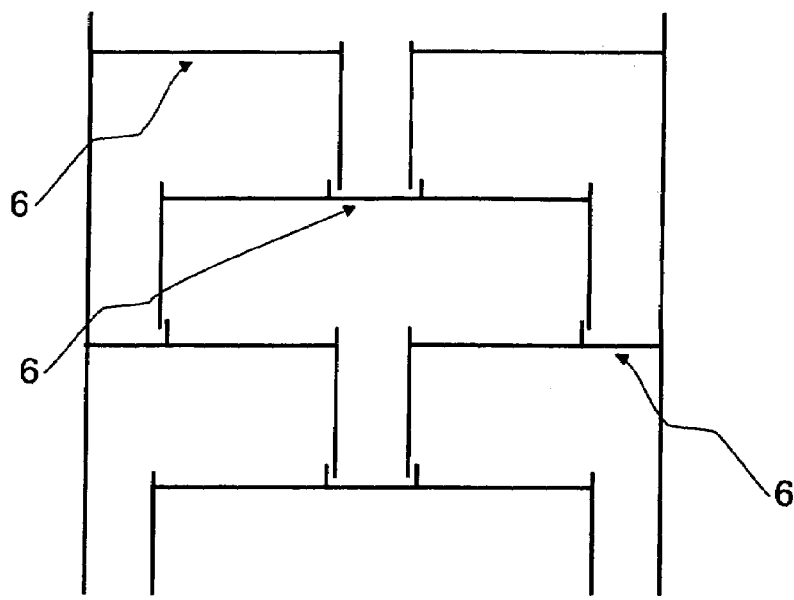
FIG. 5 is a cross-sectional view of a sequence of mass transfer trays.
Figure 6:
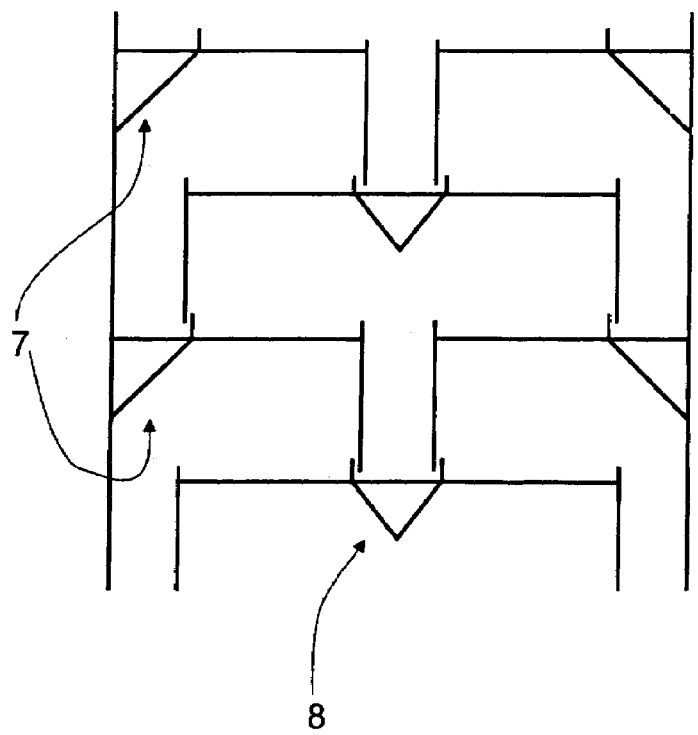
FIG. 6 is a cross-sectional view of the mass transfer trays of FIG. 5 having coverings at spray shadow areas of the trays.

In a similar manner, FIG. 5 shows a sequence of mass transfer trays with downcomers for the polymerization-inhibited reflux liquid disposed alternately at the center and side. Where the downcomer of the tray directly above opens onto the tray below, the underside of the next tray up is in the spray shadow (6), since there is normally no spraying as a consequence of insufficient pressure ratios. FIG. 6 shows how the remedy here also is simple covering (7), (8). Both the cover (7) and the cover (8) ensure the directed draining of liquid droplets which accumulate on the remaining tray underside and are entrained by the gaseous passage through the passages of the mass transfer tray directly below from the liquid phase present thereon.

The separating columns suitable for the process according to the invention may contain mass transfer trays of highly differing types. In addition to mass transfer trays, the separating internals of the separating columns suitable for the process according to the invention may also additionally be, for example, structured packings or random packings.

According to the invention, preference is given to the separating internals present in the separating columns suitable for the process according to the invention being only mass transfer trays.

For the passages of the mass transfer trays suitable for the process according to the invention, a multitude of design possibilities is known. Substantially planar orifices can be provided (sieve trays), the orifices can be provided with valves (valve trays) and the orifices can be shielded with bubble-caps against the reflux liquid (bubble-cap trays). Also suitable in accordance with the invention are more highly integrated mass transfer tray designs such as tunnel-cap and centrifugal trays in which several passages are always combined to a group of gas passages and in which the direction of the liquid stream is controlled by an impulse of the gaseous stream flowing through/out.

Otherwise, the mass transfer trays in the separating columns which are used today and have a diameter of several meters are composed of several planes which are secured on or to supports, as described, for example, by EP-A 759316.

A classic among the mass transfer trays which is particularly suitable for the process according to the invention is the sieve tray. In this document, this refers to plates whose passages for the ascending gas or vapor streams (the terms "gaseous" and "vaporous" are used synonymously in this document) are simple holes and/or slots.

The sieve trays are differentiated into two groups, i.e. into those having forced liquid flow and those without forced liquid flow.

The forced flow of the reflux liquid is achieved by the sieve trays having, in addition to the passages for the ascending gas or vapor streams, at least one downcomer (drain), through which the reflux liquid, irrespective of the flow path of the gas or vapor stream, flows from the upper tray to the next lowest tray (feed). The reflux liquid flows in crossflow over the tray from the at least one feed to the at least one drain, and the feed pipe and drainpipe guarantee the liquid seal and the desired liquid height on the tray.

Frequently (especially in the case of low column diameters), the sieve trays with forced liquid flow have a single-flow configuration. Quite generally, forced liquid flow is achieved on mass transfer trays by the mass transfer trays having at least one downcomer (drain), through which the reflux liquid flows, irrespective of the flow path of the ascending vapor stream, from the higher tray to the next lowest tray (feed). The horizontal liquid flow over the mass transfer tray from feed to drain is selected in accordance with the task in process technology terms. The rising gas stream passes through the passages of the mass transfer tray. When the reflux liquid is conducted in reverse flow over the mass transfer tray (feed and drain of the mass transfer tray are disposed on the same side of the mass transfer tray), these are referred to as reverse flow trays.

In radial flow trays, the liquid flows radially on the mass transfer tray from the middle (feed) to the drain at the edge of the tray.

In the crossflow trays, viewed over the entire flow area, the liquid is conducted transversely over the tray from feed to drain. In general, crossflow trays have a single-flow configuration. In other words, feed and drain are disposed on opposite sides of the mass transfer tray. However, they may also have a double-flow (or more than double-flow) configuration.

In this case, the feed may be disposed, for example, in the middle and a drain on each of the opposite sides of the mass transfer tray.

Preference is given to crossflow sieve trays.

In other words, feed and drain are disposed on opposite sides of the mass transfer tray. However, they may also have a double-flow (or more than double-flow) configuration. In this case, the feed may be disposed, for example, in the middle and a drain on each of the opposite sides of the mass transfer tray. In this document, such sieve trays are referred to as forced sieve trays.

In these trays, trickle-through of the reflux liquid which reduces the separating action is not, as in the case of bubble-cap trays, prevented by chimneys, in which the passages continue, but rather a minimum vapor loading is required for this purpose. The vapor rises through the passages and bubbles through the liquid layer maintained by the drainpipe.

The dual-flow or else trickle sieve trays differ from the forced sieve trays in that they contain no drain segment. The absence of drain segments (downcomers) in the dual-flow trays results in the ascending gaseous stream and the liquid stream descending in the separating column passing through the same passages of the tray. As in the case of forced sieve trays, a minimum vapor loading is also required in the case of dual-flow trays, in order to achieve appropriate separating action. When the vapor loading is significantly lower, ascending gas and descending reflux move past each other substantially without exchange and the mass transfer tray is at risk of running dry. In other words, in the case of dual-flow trays too, a lower limiting rate has to be present so that a certain liquid layer is maintained on the tray, in order to allow the tray to work.

The hydraulically sealed crossflow trays differ from the crossflow sieve trays in that, when the separating column is shut down, they cannot run dry, disregarding the tiny emptying drillhole (its cross section is normally more than 200 times smaller than the total cross section) which each crossflow tray has for reasons of utility.

In other words, even at low loadings of the separating column, hydraulically sealed crossflow trays have accumulated liquid and are at no risk of running dry. This results from the fact that the passages of hydraulically sealed crossflow trays are not chimneyless drillholes, as is the case, for example, in dual-flow trays, sieve trays and valve trays. Rather, each passage opens into a chimney which prevents the tray from running dry. Above the chimney, vapor deflecting hoods (bubble-caps) are mounted which are immersed in the accumulated tray liquid. Frequently, the vapor deflecting hoods are slotted or serrated at their edges (i.e. they have transport slots). The vapor stream rising through the passage is deflected by the vapor deflecting hoods and flows parallel to the tray, i.e. at right angles to the column, into the accumulated liquid.

The vapor bubbles leaving adjacent hoods which are generally distributed equidistantly over the tray form a froth layer in the accumulated liquid.

Drainpipes or drain segments which leave the trays, generally to the left or to the right in alternation, supported by weirs, control the liquid level of the mass transfer trays and feed the liquid to the tray below.

It is essential for the hydraulic sealing action that the drainpipes or drain segments of the upper tray are immersed in the accumulated liquid of the tray below. There are preferably no feed weirs. Bubble-caps which can be adjusted in height allow adaptation to the flow conditions and equalization of the immersion depths in the event of production irregularities, so that all bubble-caps of the tray have uniform gas flow.

Depending on the design and arrangement of the bubble-caps, the hydraulically sealed crossflow trays having single-flow configuration are divided, for example, into round bubble-cap trays (passage, chimney and bubble-cap are round), tunnel-cap trays (passage, chimney and bubble-cap are rectangular, the bubble-caps are arranged in succession, with the longer rectangular edge lying parallel to the crossflow direction of the liquid) and Thormann trays (passage, chimney and bubble-cap are rectangular, the bubble-caps are arranged in succession, with the longer rectangular edge at right angles to the crossflow direction of the liquid). Modified Thormann trays are described in DE-A 10243625.

Sieve trays differ from hydraulically sealed crossflow trays in that the flow direction of the vapor which is always upward increases the tendency to entrain small liquid drops and makes their tendency to spray the reflux liquid more marked.

The process according to the invention is therefore suitable in particular for those separating columns whose mass transfer trays are sieve trays. More preferably, their separating internals are exclusively sieve trays. Preference is given among the sieve trays to dual-flow trays. It will be appreciated that the separating columns used in the process according to the invention may also contain other mass transfer trays, for example valve trays and/or hydraulically sealed crossflow trays. The latter may also be present in the separating column together with sieve trays and/or other separating internals.

If the amount of liquid which is entrained by the rising gas stream to the underside of the next highest mass transfer tray as a proportion by weight of the total amount of liquid fed to a mass transfer tray in a separating column in inventive operation is referred to as the entrainment fraction (in % by weight) of this mass transfer tray (for definition and experimental determination, see DE-A 10300816), the process according to the invention is advantageously carried out in such a way that the entrainment fraction of at least some of the mass transfer trays is $\geq 10\%$ by weight. Frequently, the entrainment fraction of at least some of the mass transfer trays will be from $\geq 10$ to 30% by weight, or from 11 to 30% by weight, or from 12 to 30% by weight, or from 13 to 30% by weight, or from 14 to 30% by weight, or from 15 to 30% by weight. Instead of 30% by weight, other possible upper limits of the ranges mentioned are 28% by weight, or 25% by weight, or 20% by weight.

Preference is given in accordance with the invention to carrying out the thermal separating process according to the invention in such a way that the entrainment fraction of at least half of, and more preferably at least 75% of, or all, mass transfer trays of the separating column being within the aforementioned ranges.

Those mass transfer trays in particular at which the content of (meth)acrylic monomers is particularly high should be within the aforementioned ranges.

This is especially true when the separating internals of the separating column are exclusively sieve trays (forced sieve trays and/or dual-flow trays). It is especially true when the sequence of the sieve trays in the process according to the invention is equidistant.

In the process according to the invention with simultaneous elegant covering of problematic parts of the surface of internals present in the separating column, the adherence to the aforementioned boundary condition enables additionally mounted spray nozzles for polymerization-inhibited reflux liquid to be omitted entirely. However, it will be appreciated that such spray nozzles can also be used or used exclusively in the process according to the invention, for example when the separating column is operated in such a way that the entrainment fraction of all mass transfer trays present is <10% by weight.

A molecular oxygen-containing gas as a polymerization inhibitor can also be conducted through the separating column with the rising vapor or introduced into the separating column at highly varying points. In the simplest manner, such a molecular oxygen-containing gas may be air (cf., for example, DE-A 10248606, DE-A 10238142 and DE-A 10217121).

When performing the process according to the invention, if a reduction is observed in the separating action of the sequence of mass transfer trays (this term here and hereinbelow means in particular sieve trays) present in the separating column, this can be compensated by increasing the number of mass transfer trays at the same separation (i.e. the column height).

It is appropriate from an application point of view for the mass transfer tray separation within the tray sequence to vary within the range from 300 mm to 900 mm. Preference is given in accordance with the invention to the tray separation within the tray sequence in the process according to the invention being from 300 to 500 mm. In general, the tray separation should not be less than 250 mm.

The measure of increasing the number of mass transfer trays in the process according to the invention makes it possible to increase the entrainment fraction of the mass transfer trays to values of up to 70% by weight without significantly impairing the separating action. In other words, when carrying out the process according to the invention, the upper limit of the entrainment fraction of at least some of the mass transfer trays for the ranges already mentioned may, instead of 30% by weight, also be 35% by weight, or 40% by weight, or 50% by weight, or 60% by weight, or 70% by weight. It will be appreciated that the entrainment fractions of all mass transfer trays in the process according to the invention may be within this extended entrainment fraction.

Useful (meth)acrylic monomers for the process according to the invention are all of those mentioned at the outset of this document. The process according to the invention may be a fractional condensation, or a rectification, or an absorption, or a stripping, or a desorption.

In particular, the process according to the invention can be applied to all thermal processes for removing (meth)acrylic monomers from the mixtures mentioned at the outset of this document.

The content of (meth)acrylic monomers in the gaseous and/or liquid mixtures may be $\geq 2\%$ by weight, or $\geq 10\%$ by weight, or $\geq 20\%$ by weight, or $\geq 40\%$ by weight, or $\geq 60\%$ by weight, or $\geq 80\%$ by weight, or $\geq 90\%$ by weight, or $\geq 95\%$ by weight, or $\geq 99\%$ by weight.

In the case of employment of sieve trays as the mass transfer trays for the process according to the invention, they may be configured as described in DE-A 2027655, DE-A 10156988, DE-A 10230219, EP-A 1029573 or in Grundlagen der Dimensionierung von Kolonnenböden [Guidelines for dimensioning column trays], Technische Fortschrittsberichte [Technical progress reports], volume 61, K. Hoppe, M. Mittelstrass, Verlag Theodor Steinkopff, Dresden 1967. The passages may be circular, elliptical or rectangular. They may also have any other shape (for example slot-shaped). Preference is given in accordance with the invention to them being circular and arranged in strict triangular pitch. For example, the hole diameter of the sieve trays (especially in the case of dual-flow trays) may be from 5 to 50 mm, preferably from 10 to 25 mm. The separation of two adjacent hole centers is appropriately from 1.5 to 3 times, preferably from 2 to 2.8 times, the hole diameter, which is preferably dimensioned uniformly over the individual sieve trays.

The orifice ratio (ratio of the total surface area of all passages of the sieve tray to the total surface area of the sieve tray multiplied by 100 and in %) in sieve trays to be used in accordance with the invention is appropriately from 8 to 30% and frequently from 12 to 20%. The tray thickness is advantageously from 1 to 8 mm.

Processes according to the invention are, for example, rectifications or fractional condensations which are carried out in separating columns whose separating internals are exclusively trays of whose number at least two, preferably more than two (preferably $\geq 10\%$, or $\geq 20\%$, or $\geq 30\%$, or $\geq 40\%$, or $\geq 50\%$, or $\geq 60\%$, or $\geq 75\%$), and more preferably all, sieve trays are particularly advantageously dual-flow trays having circular passages.

The remaining trays may, for example, be hydraulically sealed crossflow trays (for example Thormann trays or bubble-cap trays) and/or valve trays.

The gas loading factor F of the sequence of sieve trays to be employed in accordance with the invention is in practice in many cases in the range from 1 to 3 $Pa^{0.5}$, frequently in the range from 1.5 to 2.5 $Pa^{0.5}$. The liquid flow rate is simultaneously often in the range from 1 to 50 m/h or in the range from 2 to 10 m/h.

As already mentioned, the process according to the invention is operated with polymerization inhibition. To this end, the polymerization inhibitors are generally introduced at the top of the separating column into the liquid phase descending in the separating column (for example the reflux liquid or the absorbent). Typical polymerization inhibitors to be used in accordance with the invention are phenothiazine, 4-hydroxy-2,2,6,6-tetramethylpiperidine N-oxyl, hydroquinone and the monomethyl ether of hydroquinone (4-methoxyphenol). As a further stabilization measure, a molecular oxygen-containing gas, for example air, can additionally, as likewise already described, be conducted through the separating column. In favorable cases, polymerization can even be inhibited exclusively with air.

In dual-flow trays used in accordance with the invention, transverse mixing and large-surface-area wave movements on the dual-flow trays are advantageously prevented by perpendicular, flat internals, known as baffles. From an application point of view, the baffles in their industrial scale use are appropriately from 50 to 300 mm, preferably from 150 to 200 mm high, and from 500 to 6000 mm, preferably from 1000 to 3000 mm long (their length may be equal to the tray diameter or part of the tray diameter). Their lower edge preferably does not rest directly on the upper side of the dual-flow tray, but rather they are supported by means of small feet or separators on the dual-flow tray in such a way that the separation of their lower edge to the upper side of the dual-flow tray is from 10 to 60 mm, preferably from 30 to 50 mm. The number of separators per baffle is from 1 to 10. From an application point of view, the separation of the baffles is appropriately from 100 to 1000 mm, frequently from 150 to 500 mm. The surface segments between two baffles are normally $\geq 0.2$ m$^2$, but usually $\geq 5$ m$^2$, which limits the number of baffles per dual-flow tray.

The aforementioned measures are suitable in particular for a preferred embodiment of the dual-flow trays of the example and comparative example in the documents DE-A 10243625 und DE-A 10247240.

An increase in the entrainment fraction in a separating column to be operated in accordance with the invention is possible in a simple manner, for example, by covering some of the passages of the mass transfer trays at constant loading.

It will be appreciated that the process according to the invention can also be employed in combination with some or all of the measures which are mentioned in the documents DE-A 2027655, EP-A 937488, EP-A 1044957 and EP-A 1029573 and reduce undesired polymerization.

Quite generally, the process according to the invention can be carried out under atmospheric pressure, elevated pressure or under reduced pressure.

In particular, the process according to the invention is suitable for the fractional condensations described in DE-A 19924532, DE-A 10243625 and DE-A 10247240 of product gas mixtures which comprise acrylic acid and are from heterogeneously catalyzed gas phase partial oxidations of $C_3$ precursors of acrylic acid with molecular oxygen in separating columns which, from bottom to top, contain initially dual-flow trays followed by hydraulically sealed crossflow mass transfer trays.

The process according to the invention is characterized by a reduced tendency toward undesired polymer formation.

It will be appreciated that even in the process according to the invention, excessively high gas loading factors or liquid flow rates no longer allow the liquid to drain sufficiently from the sieve trays, and the mass transfer trays can flood. Beyond the flooding limit, no viable column operation is possible.

In general, the mass transfer trays used, in particular dual-flow trays used, in the process according to the invention are joined flush to the column walls. However, there are also embodiments in which there is an intermediate space between column wall and tray which is only partly interrupted by bridges. In addition to the actual passages, dual-flow trays used in the process according to the invention, if need be, have further orifices which enable, for example, the tray to be secured to support rings or the like (cf., for example, DE-A 10159823).

The process according to the invention is suitable in particular also for the rectification described by way of example in DE-A 10230219, and also for the absorption described in EP-A 925272 in stage (b).

The separating columns according to the invention and also the internals disposed therein are appropriately manufactured from stainless steel (e.g. 1.4541 or 1.4571 or SUS 316L).

For the inventive covering, it is appropriate to use stainless steel sheets of the same type which are welded. Very thin sheets are selected, although the mechanical stability has to be ensured and excessively thin sheets can only be welded with difficulty. Typically, the sheets used have a thickness of from 0.5 to 5 mm, preferably from 1 to 3 mm.

When separate spray nozzles are integrated into the separating column in the process according to the invention, their number can be limited, i.e. minimized, as a consequence of the procedure according to the invention.

EXAMPLE AND COMPARATIVE EXAMPLE

1. Comparative Example

In a rectification column having internal diameter 3.8 m and length 32 m, a mixture was separated which contained the following constituents:

| | |
|---|---|
| 17 | % by weight of acrylic acid, |
| 0.02 | % by weight of water, |
| 0.0015 | % by weight of acrolein, |
| 0.0015 | % by weight of allyl acrylate, |
| 0.01 | % by weight of furfural, |
| 0.027 | % by weight of acetic acid |
| 0.2 | % by weight of benzaldehyde, |
| 0.003 | % by weight of propionic acid, |
| 0.032 | % by weight of maleic anhydride, |

-continued

| | |
|---|---|
| 58 | % by weight of Diphyl ® (mixture of approx. 25% by weight of diphenyl and approx. 75% by weight of diphenyl ether), |
| 17 | % by weight of dimethyl phthalate, |
| 3 | % by weight of acryloylpropionic acid and |
| 300 | ppm by weight of phenothiazine. |

The separating internals of the rectification column were 46 dual-flow trays which were arranged equidistantly. The tray separation was 400 mm. The mixture to be separated was fed into the rectification column at the 8th tray from the bottom. Below the feed, the diameter of the circular passages in the dual-flow trays was 50 mm. Above the feed, the diameter was 25 mm. The passages in the dual-flow trays were arranged in strict triangular pitch (cf. DE-A 10230219). The overall orifice ratio (the gas-permeable surface area in the tray surface as a proportion of the total surface area of the tray surface) below the feed was 17.8% and above the feed was 12.6%. The temperature at the top of the column was 80° C., the pressure 105 mbar and the reflux ratio 1.3.

The temperature at the bottom of the column was 193° C. The pressure above the bottom surface was 230 mbar. The column bottom was heated with a forced-circulation evaporator. The reflux of the rectification column was polymerization-inhibited by adding phenothiazine to such an extent that the product which was withdrawn in the sidestream from the rectification column contained 250 ppm by weight of phenothiazine. For the purpose of polymerization inhibition, 600 000 l(STP)/h of air were additionally introduced into the lower section of the rectification column. The feed into the rectification column had a temperature of 152° C.

At the top of the column, a low boiler mixture containing 96% by weight of acrylic acid was withdrawn. A low boiler mixture was continuously withdrawn from the bottom of the rectification column and contained less than 0.5% by weight of acrylic acid. Below the 40th tray from the bottom, 99.6% by weight acrylic acid was withdrawn as the product in a sidestream.

To support the dual-flow trays, two double-T supports were used per tray in the rectification column. The transverse limb of the Ts was 120 mm wide, and the longitudinal limb connecting the two transverse limbs was 240 mm high. The thickness of the limbs was 10 mm.

After a running time of 40 days, the double-T supports were covered with polymer.

2. Example

The procedure of the comparative example was repeated, except that the double-T supports were covered with steel sheet in accordance with FIG. 2. The sheet thickness was 2 mm. The sheets were welded at the edges. After a running time of 40 days, the covered double-T supports were still free of polymer.

We claim:

1. A process for the thermal separation of (meth)acrylic monomer, comprising:

ascending at least one gaseous stream in a separating column containing a sequence of mass transfer trays and a liquid stream that contains dissolved polymerization inhibitor which descends the separating column, at least one of said streams comprising (meth)acrylic monomers; and spraying the inner surface of the separating column with the descending liquid stream that contains the dissolved polymerization inhibitor, and the separating column having internals, certain areas of which are shadow regions of the sprayed descending liquid stream; and which shadow regions are equipped by covering means which prevent contact of the shadow regions with (meth)acrylic monomers and consequently undesired polymerization of monomer.

2. The process as claimed in claim 1, wherein the inner surface of the separating column is sprayed with the liquid stream descending the separating column by the gaseous stream moving upward, as it passes through mass transfer trays, thereby entraining small liquid droplets from the liquid phase disposed thereon and spraying them upward into the column.

3. The process as claimed in claim 2, wherein the internals are double-T supports whose the shadow regions are equipped by covering means.

4. The process as claimed in claim 2, wherein the internals are double-U supports whose shadow regions are equipped by covering means.

5. The process as claimed in claim 2, wherein the mass transfer trays are sieve trays.

6. The process as claimed in claim 2, wherein at least some of the mass transfer trays have an entrainment fraction of at least 10% by weight up to 30% by weight.

7. The process as claimed in claim 1, wherein the internals are double-T supports whose shadow regions are equipped by covering means.

8. The process as claimed in claim 1, wherein the internals are double-U supports whose shadow regions are equipped by covering means.

9. The process as claimed in claim 1, wherein the mass transfer trays are sieve trays.

10. The process as claimed in claim 1, wherein the gaseous stream and/or liquid stream is comprised of at least 2% by weight (meth)acrylic monomer.

11. The process as claimed in claim 10, wherein the gaseous stream and/or liquid stream is comprised of at least 10% by weight (meth)acrylic monomer.

* * * * *